United States Patent [19]

Sheehan

[11] Patent Number: 5,053,038
[45] Date of Patent: Oct. 1, 1991

[54] COMPRESSION BONE STAPLE
[75] Inventor: Joseph C. M. Sheehan, Oak Park, Ill.
[73] Assignee: Tenstaple, Inc., Malvern, Pa.
[21] Appl. No.: 395,315
[22] Filed: Aug. 17, 1989
[51] Int. Cl.⁵ ............................................. A61F 5/04
[52] U.S. Cl. ..................................................... 606/75
[58] Field of Search .................. 606/75, 77; 411/450, 411/456, 457, 458, 459, 460, 471, 475, 477, 478

[56] References Cited

U.S. PATENT DOCUMENTS

| | | | |
|---|---|---|---|
| 2,632,356 | 3/1953 | Thiel | 411/471 |
| 3,618,447 | 11/1971 | Goins | 411/456 |
| 3,807,394 | 4/1974 | Attenborough | 606/75 |
| 3,939,828 | 2/1976 | Mohr et al. | 606/75 |
| 4,399,810 | 8/1983 | Samuels et al. | 411/457 |
| 4,434,796 | 3/1984 | Karapetian et al. | 606/75 |
| 4,570,623 | 2/1986 | Ellison et al. | 606/75 |
| 4,838,254 | 6/1989 | Gauthier | 606/75 |
| 4,841,960 | 6/1989 | Garner | 606/75 |

Primary Examiner—Robert A. Hafer
Assistant Examiner—Charles H. Sam
Attorney, Agent, or Firm—Kane, Dalsimer, Sullivan, Kurucz, Levy, Eisele and Richard

[57] ABSTRACT

A compression surgical staple for bone to bone fixation along a fracture line includes spring means for driving the fractured interfaces together.

4 Claims, 4 Drawing Sheets

COMPRESSION BONE STAPLE

BACKGROUND OF THE INVENTION

1. Field of the Invention

The invention relates to surgical staples and more particularly to a surgical staple having advantages in orthopedic surgery for repairing bone fractures and like defects.

2. Brief Description of the Prior Art

The simplicity of using a surgical staple has always been attractive to the orthopedic surgeon, the potential speed of their insertion being an obvious advantage over the use of bone screws. In fact, staples have been used by the orthopedic surgeon to repair bone fractures since the early 1940's. With the development of physiologically acceptable materials such as stainless steels, it became possible to leave the staple in place after the bone fracture healed.

As materials for fabricating staples developed, the Chrome-Cobalt series of heavier, harder staples became available, having some advantages. However, these staples have a greater use for the reattachment of ligaments to bone than for use in bone to bone fixation of fractures.

The Coventry staple was developed for fixing osteotomies and maintaining bone positions while an external cast was applied. This was the first serious recognition and use of a staple as a means of bone to bone fixation.

In more recent years the Shapiro staple with the aid of a power inserter has enabled the orthopedic surgeon to rapidly insert a plurality of staples into bone, to fix the fractured surfaces into position for healing.

However, the use of staples for bone to bone fixation along a fracture line has not won complete acceptance by the surgeon. In the early uses, insertion of the staple was carried out with a simple holding instrument and a hammer to drive the staple legs into the bone. This often caused the separate bone moieties to move from their desired positions before completion of the insertion. The use of the power driven hammer and the Shapiro staple did not completely obviate this problem even though the increased speed of insertion might be expected to alleviate it.

The correct positioning of the fractured surfaces of a bone is important to promote healing. A fracture is generally accompanied by a hemorrhaging of the periosteum at the fracture site. Fibroblasts and capillaries grow into the resulting blood clot to form granulation tissue and plasma and white blood cells exude into the tissue to form a viscous callus which serves to adhere the fractured bone surfaces together during the healing process. Bone cells from the periosteum and calcium salts are deposited in the callus to harden and form new bone. Ideally, to speed ossification the bone interfaces at the fracture site are held together under compressive forces. Otherwise, if the interfaces are held apart either under neutral or tension forces, fibrous ingrowth may occur rather than new bone development. This condition, known as "fibrous union", represents a failure of treatment. For this reason, the orthopedic surgeon has been wary of using staples to achieve bone to bone fixation in many circumstances.

In the absence of a reliable stapling procedure, the art presently resorts to fixation means and devices which permit the surgeon to place the fractured bone interfaces together under compression. Compression is obtained either after inserting the device and requiring the patient to put pressure on the bones (for example with application of the Richards hip screw or the Kutchner intramedullar rod) or by mechanically adding compression via a screw mechanism (such as in compression plates, dynamic compression plates or external fixation devices; see also the compression nail device described in U.S. Pat. No. 4,574,795). It will be appreciated that these procedures require major instrumentation and operative skills with significant surgical exposure and risk.

Also representative of prior art bone staples are those described in U.S. Pat. No. 4,570,623 and in the European Patent Application 0 301 896, both of which describe staples with serrated or toothed legs.

The staple and method of the present invention represents an improvement in the orthopedic arts, permitting bone stapling to achieve bone to bone fixation under compression of the fracture interfaces. The procedure is simple, quick and efficient, minimizing surgical exposure and risks. The staple and method of the invention can be used to fix even small, multiple fragmented bone fractures employing a series of staple insertions.

SUMMARY OF THE INVENTION

The invention comprises a compression bone staple, which comprises;
(a) an elongate bridge member having
 (i) a first end;
 (ii) a second end;
 (iii) an elongate body between the first and second ends;
(b) a first leg comprising an elongate body having a first leg first end and a first leg second end, said second end including a bone penetrating point;
(c) a second leg comprising an elongate body having a second leg first end and a second leg second end, said second leg second end including a bone penetrating point;
(d) first spring means hingedly connecting the first end of the first leg to the first end of the bridge member;
(e) second spring means hingedly connecting the first end of the second leg to the second end of the bridge member;
said first and second legs being spaced from the bridge member and extending away from the bridge member in planes transverse to the axial plane of the bridge member; said first ends of the first and second legs being spaced apart from each other a distance less than the length of the bridge member;
said bone penetrating points of the first and second legs being in the same plane, said same plane being substantially parallel to the axial plane of the bridge member.

The invention also comprises a process of treating bone fractures, which comprises bone fixation under compression of the fractured bone surfaces, using the surgical staple of the invention.

DETAILED DESCRIPTION OF THE PREFERRED EMBODIMENTS OF THE INVENTION

Those skilled in the art will gain an appreciation of the invention from a reading of the following description of preferred embodiments of the invention when read in conjunction with a viewing of the accompanying drawings of FIGS. 1-7, inclusive.

Figures 1, 2:
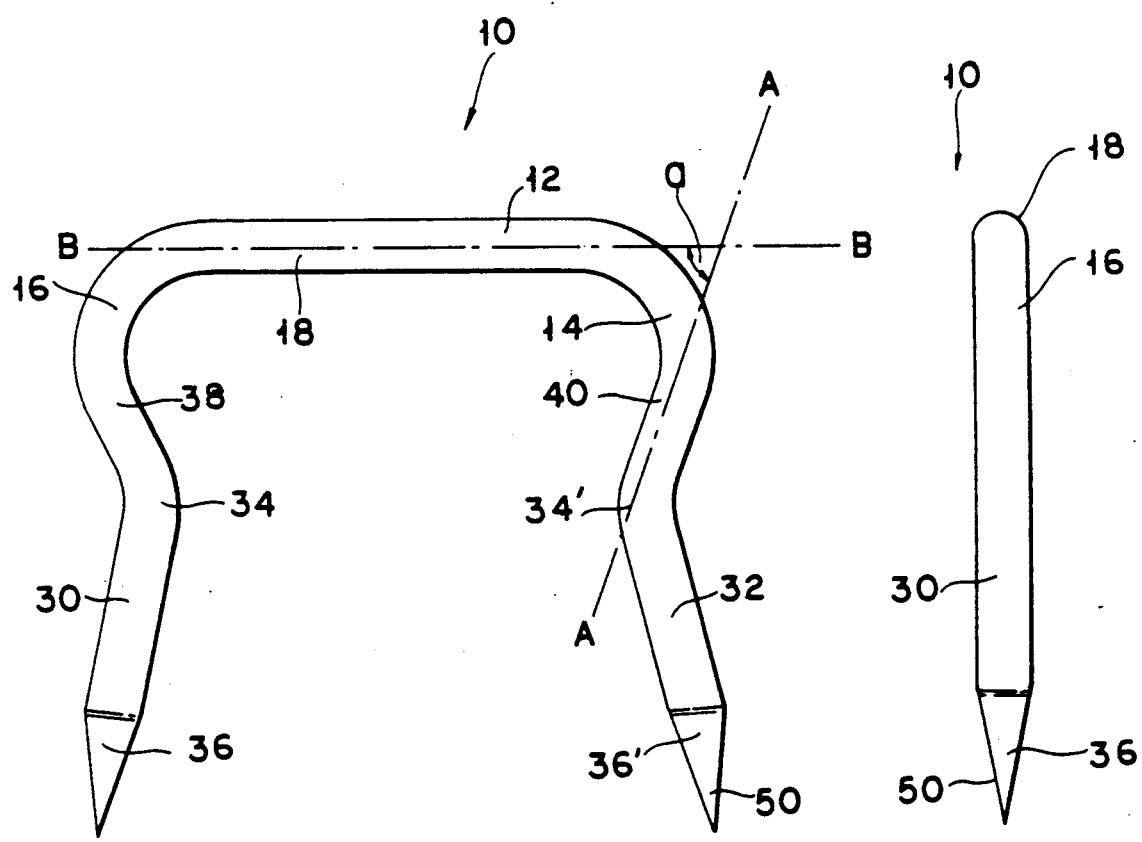
FIG. 1 is a side view (enlarged) of an embodiment compression surgical staple of the invention.
FIG. 2 is an end view of the staple shown in FIG. 1.

Referring first to FIG. 1, there is seen a side view, enlarged, of an embodiment compression staple 10 of the invention. The staple 10 comprises an elongate bridge member 12 having a first end 14 and a second end 16 with an elongate body 18 between the ends 14,16. The body 18 is a round wire, although it may have any cross-sectional configuration including that of a flat strip having an upper planar surface and a lower planar surface bounded by a peripheral edge. The body 18 between ends 14,16 has a substantially straight axis (broken line B—B) extending between the downward bend at end 14 to the downward bend at end 16. The ends 14, 16 are part of the bridge member 12 and mark the outer limits of the overall width of staple 10 at the bridge 12 end thereof. In the embodiment staple 10 the ends 14,16 (and therefore bridge 12) are bent downward equally, but they need not be so bent. Bridge 12 may be straight from end to end, including ends 14, 16. The bridge member 12 of staple 10 preferably provides the maximum dimensions, sidewise, of the staple 10.

Staple 10 legs 30,32 are elongate, cylindrical, non-serrated (smooth, untoothed) members, each having a first end 34 or 34' and a second end 36 or 36'. The second ends 36,36' include bone penetrating points 50 which will be described in greater detail hereinafter.

Legs 30,32 are connected through their respective first ends 34,34' to the bridge member 12 ends 14,16, respectively via an intermediate leaf spring. The spring 38 connects hingedly leg 30 end 34 to end 14 of bridge member 12 and spring 40 connects hingedly leg 32 end 34' to the end 16 of bridge member 12. The springs 38,40 flex independently at the points of connection so that the relative positions of the bridge member 12, springs 38,40 and legs 30,32 may be changed by imposing a force on the springs 38,40 while holding the bridge member 12 and/or legs 30,32 in substantially fixed relative positions. The spring means 38, 40 may be structured separate components of staple 10 or may be integral and unitary with bridge 12 and legs 30, 32 as shown in FIG. 1, but they have a functional separateness.

Figure 3:
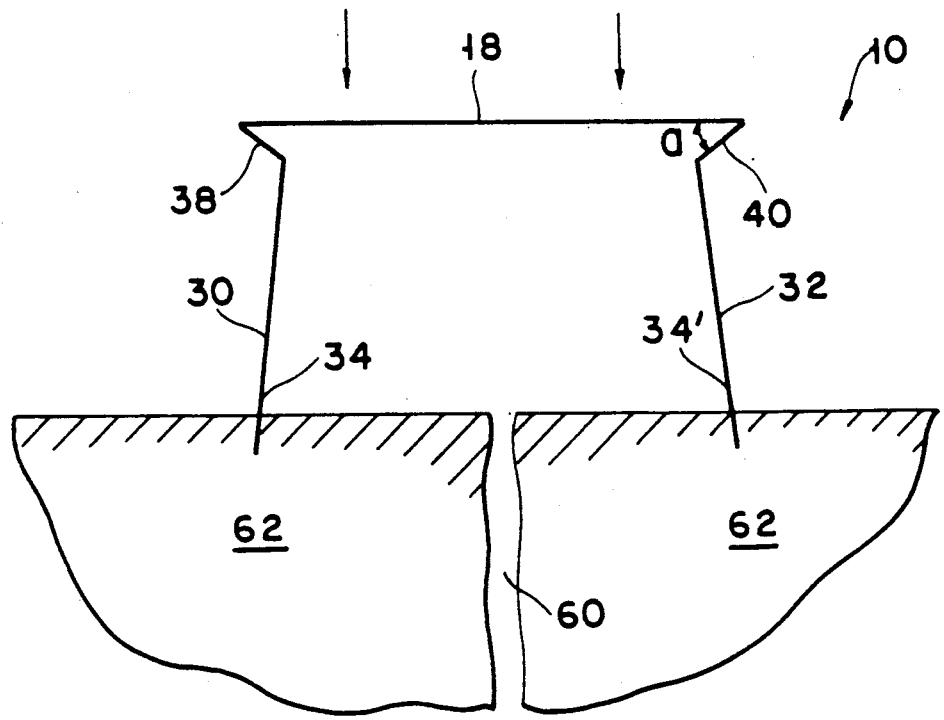
FIG. 3 is a stylized side elevation of the staple shown in FIG. 1, partially inserted at the site of a bone fracture.

As may be seen in FIGS. 1 and 2 and more clearly in FIG. 3, a stylized side elevation of the compression staple 10, the legs 30,32 extend in a direction generally downward and away from the bridge member 12 in separate planes, each plane being transverse to the axial plane along line (B—B) of the bridge member 12 and each other. The legs 30,32 are straight, smooth and spaced apart from each other, of substantially equal lengths and have axial planes transverse to each other and to line B—B. However, legs 30,32 may extend parallel to each other. The ends 34,34' are spaced apart from each other a distance less than the length of body 18 of bridge member 12 so that the straight springs 38,40 each extend inwardly along axial lines A—A towards each other from their respective connections at ends 14,16 of the bridge member 12, thereby forming an acute angle "a" with the bridge member 12. This angle is of importance as will be described more fully hereinafter. Suffice it to say at this time that the angle "a" is advantageously within the range of from about 65° degrees to about 78° degrees. For use with the hardest bones, angle "a" is advantageously greater than about 72° degrees, to avoid collapse of the angle during initial staple insertion.

Figure 6:
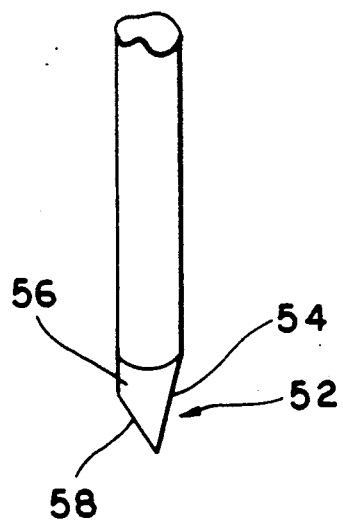
FIG. 6 is an enlarged view of a preferred embodiment bone penetration point on the legs of the staple shown in FIGS. 1-5.

The ends 36,36' are spaced apart from each other a distance equal to or greater than the distance between ends 34,34'. The ends 36,36' each include bone penetrating points 50. The compression strength of compact bone is within the range of from about 18,000 to about 24,000 psi. Bone is a viscoelastic material, and penetration is more effectively achieved with, for example, a trochoid point 50 as shown in FIGS. 1 and 2. However, a blade point 52 as shown in FIG. 6 includes three beveled faces 54, 56, 58 for cutting compact bone tissue as insertion proceeds (face 58 not seen in FIG. 6).

Figures 7, 8:
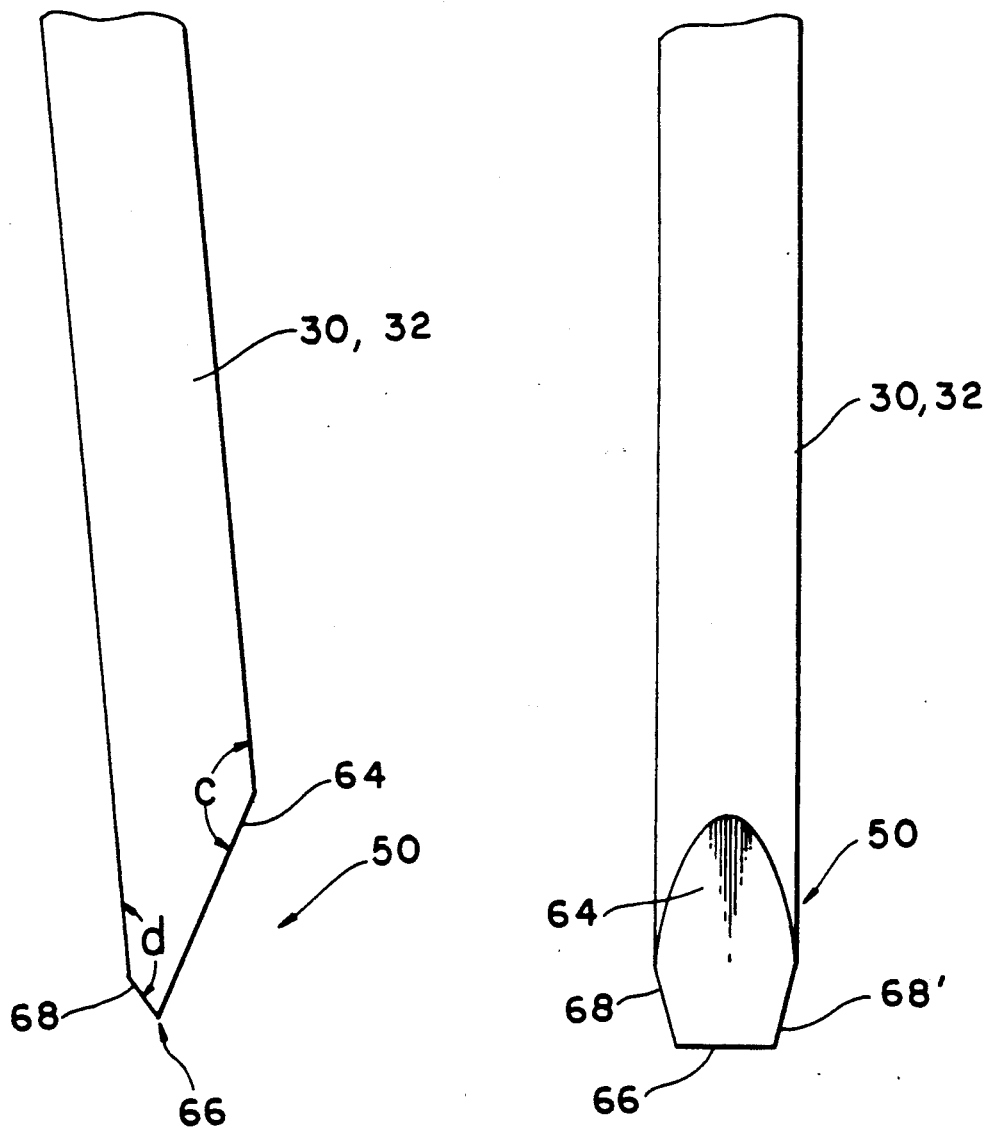
FIG. 7 is a view of a preferred bone penetration point.
FIG. 8 is a side view of the bone penetration point shown in FIG. 7.

FIG. 7 is a view of a preferred bone penetrating point 50 on each leg 30, 32 the point 50 is a bone cutting wedge made by a bevel face 64 formed by grinding the legs 30, 32 at an angle "c" of about 145° to 155°. A sharp edge 66 is formed by an intersecting face 68, which is a bevel cut of about 128° to 135° (angle "d"). Advantageously the length of face 68 is about 0.10 inches (±0.005"). Advantageously the face 64 has a length of about 0.046 inches (±0.010"). FIG. 8 is a side view of the point 50 shown in FIG. 7 (rotated 90°) and shows more clearly the wedge of chisel edge 66 between face 68 and a matching face 68' opposite face 68. The point 50 shown in FIGS. 7 and 8 facilitates cutting into bone surfaces, provides a stable surface for contact and facilitates the making of a bore in the bone to receive the spring means described above.

Figure 4:
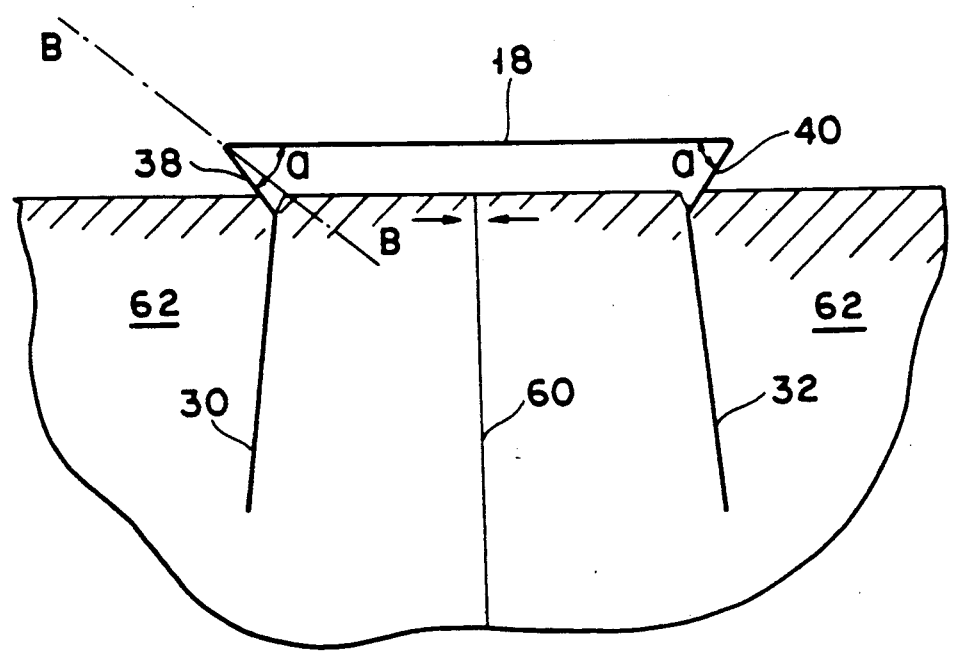
FIG. 4 is a view as in FIG. 3, as the spring means enters the bone during insertion.
Figure 5:
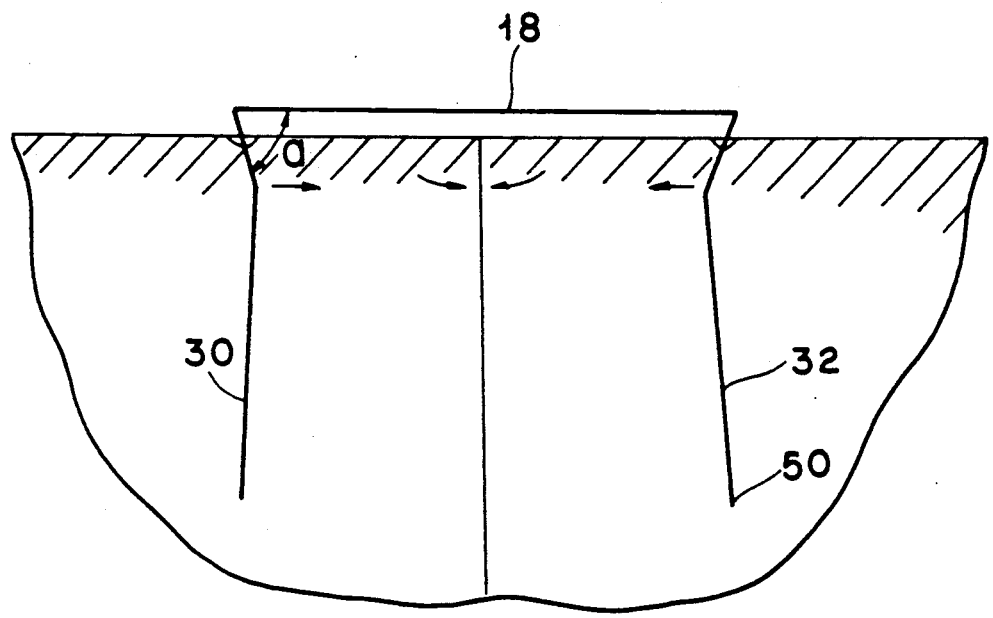
FIG. 5 is a view as in FIGS. 3 and 4, upon completion of staple insertion.

The method of the invention will now be described with reference to the drawings of FIGS. 3-5, inclusive. Referring first to FIG. 3, there is seen a stylized side view of staple 10, partially inserted at the site of a long bone fracture. Bone penetration points 50 have made an initial penetration. The legs 30, 32 and bridge 12 straddle a transverse fracture 60 of a long bone 62. The fracture 60 has separated the two bone 62 fracture interfaces. As shown in FIG. 3, staple 10 is being hammered in the direction of the arrows, the bone penetration points of legs 30,32 ends 34,34' having penetrated partially the compact bone. Hammering is preferably accomplished with the aid of a powered bone staple inserter (spring or air powered). Such inserters are well known (see for example descriptions in the U.S. Pat. Nos. 4,415,111; 4,500,025; 4,527,726; and 4,569,469) and commercially available bone staple inserters may be adapted to insert the bone staple of the present configuration. However, a simple hammer can be used. As the staple legs 30,32 continue to penetrate the bone 62, under a hammering, their oblique axial planes force the bone 62 on each side of fracture 60 to pull together, closing the fracture and compressing the bone interfaces upon each other. Then, the springs 38,40 follow into the driven bores established by passage of the legs 30,32. As shown in FIG. 4, the springs 38,40 have partially entered the aforesaid bores, causing an opening and an increase of the angle "a" and the imposition of a tensioning force on each spring 38,40, the springs 38,40 being forced from their normal position as shown by the broken lines C—C are biased towards each other. The bias force of the tension loaded springs 38,40 is exerted against the bone, and towards each other causing a further compression of the fractured interfaces together (see the arrows pointing toward the fracture line 60), holding closed the fracture 60 under pressure. It is important that the spring 38, 40 portions at the connection with bridge member 12 be free and not driven into the bone so that the spring action is not lost. Upon healing of the fracture, the staple 10 can be left in place if desired.

The staple 10 may be fabricated from any physiologically acceptable surgical material such as titanium, or a stainless surgical steel. Preferably stainless steel 316 L is used.

Those skilled in the art will appreciate that many variations and departures may be made from the above-described preferred embodiments of the invention without departure from the scope of the following claims. For example, although the surgical staple 10 described above fabricated from continuous, flat strips with planar surfaces or they may be built up from separate structural components. Although the embodiment staple 10 as shown in the accompanying drawings has round wire legs 30, 32 legs may advantageously be non-round, for example of a triangular, elliptical or other cross-sectional configuration. Preferably however, the staple of the invention is a unitary, continuous length of round wire, having a diameter within the range of from about 0.020" to about 0.050"; most preferably about 0.030".

The dimensions of the surgical staples of the invention may also be widely varied to meet specific bone repairs. As an example, the leg 30,32 length may be within the range of from about 0.2 to about 0.45 inches. The legs 30,32 will generally be equal in length, but need not be. In fact, in some special circumstances it may be advantageous to employ legs 30,32 of unequal length. For example, when the anatomy of the bone's surface presents a surface which is not level.

The bridge 12 of the staple 10 may vary widely in length and is governed only by the availability of a bone insertion site on each side of the fracture to be fixed.

What is claimed is:

1. A compression bone staple, which comprises;
   (a) an elongate bridge member having
      (i) a first end;
      (ii) a second end;
      (iii) an elongate body between the first and second ends;
   (b) a first leg comprising an elongate body having a first leg first end and a first leg second end, said second end including a bone penetrating point;
   (c) a second leg comprising an elongate body having a second leg first end and a second leg second end, said second leg second end including a bone penetrating point;
   (d) first spring means hingedly connecting the first end of the first leg to the first end of the bridge member;
   (e) second spring means hingedly connecting the first end of the second leg to the second end of the bridge member;
   each of said first and second spring means extending towards each other from their respective connections with the bridge member;
   said first and second legs being spaced from the bridge member and extending away from the bridge member in planes transverse to the axial plane of the bridge member; said first ends of the first and second legs being spaced apart from each other a distance less than the length of the bridge member;
   said bone penetrating points of the first and second legs being in the same plane.

2. A process for fixing the fractured ends of a mammalian bone together to promote healing of the fracture, which comprises:
   I. providing a compression bone staple, which comprises:
      (a) an elongate bridge member having
         (i) a first end;
         (ii) a second end;
         (iii) an elongate body between the first and second ends;
      (b) a first leg comprising an elongate body having a first leg first end and a first leg second end, said second end including a bone penetrating point;
      (c) a second leg comprising an elongate body having a second leg first end and a second leg second end, said second leg second end including a bone penetrating point;
      (d) first spring means hingedly connecting the first end of the first leg to the first end of the bridge member;
      (e) second spring means hingedly connecting the first end of the second leg to the second end of the bridge member;
      each of said first and second spring means extending towards each other from their respective connections with the bridge member;
      said first and second legs being spaced from the bridge member and extending away from the bridge member in planes transverse to the axial plane of the bridge member; said first ends of the first and second legs being spaced apart from each other a distance less than the distance between the first and second ends of the bridge member;
      said bone penetrating points of the first and second legs being in the same plane;
   II. reducing the fracture;
   III. positioning the staple on the surface of the bone, astraddle the fracture site with the first leg on one side of the fracture and the second leg on the other side of the fracture;
   IV. inserting the first and second legs of the positioned staple into the bone surface, whereby a bore is made by each leg inserted; and
   V. forcing the first and second spring means into said bores;
      whereby each of said first and second spring means is placed under tension and biased towards each other.

3. The staple of claim 1 wherein each of the first and second spring means forms an acute angle of from about 65° to about 78° with the bridge member.

4. The process of claim 2 wherein each of the first and second spring means forms an acute angle of from about 65° to about 78° with the bridge member.

* * * * *